United States Patent
Park et al.

(10) Patent No.: US 10,909,627 B2
(45) Date of Patent: *Feb. 2, 2021

(54) MULTIPLE COMPUTER SERVER SYSTEM FOR ORGANIZING HEALTHCARE INFORMATION

(71) Applicant: BIOPOLICY INNOVATIONS INC., Vancouver (CA)

(72) Inventors: Andrew Park, Blaine, WA (US); Drew Gutschmidt, Vancouver (CA)

(73) Assignee: Biopolicy Innovations Inc., Vancouver (CA)

( * ) Notice: Subject to any disclaimer, the term of this patent is extended or adjusted under 35 U.S.C. 154(b) by 955 days.

This patent is subject to a terminal disclaimer.

(21) Appl. No.: 14/265,118

(22) Filed: Apr. 29, 2014

(65) Prior Publication Data
US 2014/0324449 A1 Oct. 30, 2014

(30) Foreign Application Priority Data
Apr. 29, 2013 (CA) ..................................... 2814365

(51) Int. Cl.
*G16H 70/20* (2018.01)
*G06Q 40/08* (2012.01)
*G06Q 10/10* (2012.01)

(52) U.S. Cl.
CPC .............. *G06Q 40/08* (2013.01); *G06Q 10/10* (2013.01); *G16H 70/20* (2018.01)

(58) Field of Classification Search
CPC ........ G06Q 50/22; G06Q 50/24; G06Q 10/10; G06Q 40/08; G06F 17/241; G06F 17/243

USPC ............................................................ 705/2
See application file for complete search history.

(56) References Cited

U.S. PATENT DOCUMENTS

| | | | |
|---|---|---|---|
| 7,860,735 B2 | 12/2010 | Evanitsky | |
| 8,218,887 B2 | 7/2012 | Zyuzin | |
| 8,364,688 B1* | 1/2013 | Thomas | ................. G06Q 10/10 707/709 |
| 9,311,399 B2* | 4/2016 | Thomas | ............ G06F 17/30861 |
| 2002/0120776 A1 | 8/2002 | Eggebraaten et al. | |
| 2003/0219709 A1 | 11/2003 | Olenick et al. | |
| 2003/0233278 A1 | 12/2003 | Marshall | |
| 2005/0171947 A1* | 8/2005 | Gautestad | ............. G06F 16/958 |
| 2005/0187948 A1 | 8/2005 | Monitzer et al. | |
| 2006/0293923 A1 | 12/2006 | Farris | |
| 2008/0059224 A1 | 3/2008 | Schechter | |
| 2008/0177994 A1* | 7/2008 | Mayer | ................... G06F 9/4418 713/2 |
| 2008/0221936 A1 | 9/2008 | Patterson | |
| 2011/0112873 A1 | 5/2011 | Allen et al. | |

(Continued)

*Primary Examiner* — Hiep V Nguyen
(74) *Attorney, Agent, or Firm* — Stites & Harbison, PLLC; Jeffrey A. Haeberlin

(57) ABSTRACT

A method of providing changes in healthcare policy information is provided, including: maintaining a first database, the first database containing records including copies of websites, the websites pertaining to policy information; a first server scanning current versions of the websites on the Internet and identifying which of the websites have been changed to a second server; and updating the records in the first database; a second server generating a report of the changes made to each of the identified websites; and the second server providing access to a user to generate reports relating to the websites.

8 Claims, 8 Drawing Sheets

(56) References Cited

U.S. PATENT DOCUMENTS

| | | |
|---|---|---|
| 2012/0078651 A1 | 3/2012 | Henderson et al. |
| 2012/0271657 A1* | 10/2012 | Anderson ............ G06F 17/243 |
| | | 705/4 |
| 2013/0290270 A1 | 10/2013 | Pareek |
| 2014/0142989 A1 | 5/2014 | Grosso |

* cited by examiner

Search Page for Data Report

Master

Therapy

Therapy Category

Therapy Subcategory

Select Policies to Compare

Cervarix
Gardasil

Select All

Select Payer(s)

Cigna
Humana
Payer 3
Payer 4

Select Data Points

> Coverage
> Formulary Tier
> Coding
> Review Date
> Quantity Limit
> Step-Therapy
> Co-Pay
> Additional User-Defined Comparable Fields > Plan Name
> Covered Lives Create Report

FIG. 5a

Output from 5a

[Report Results]

|  | Cigna | Humana | Payer 3 | Payer 4 |
|---|---|---|---|---|
| Coverage | Yes |  | Yes | Yes |
| Next Review Date | 2013-10-15 |  | 2014-02-03 | 2013-06-28 |
| Formulating Tier |  |  | 4 | 5 |
| Coding | 90649<br>V04.89 |  | 90649<br>90650 | Vo1.6<br>Vo2.8<br>V69.2 |
| Policy | Gardasil |  | Gardasil | Gardasil |
| Additional User-Defined Comparable Fields | --- | --- | --- | --- |

FIG. 5b

MULTIPLE COMPUTER SERVER SYSTEM FOR ORGANIZING HEALTHCARE INFORMATION

FIELD OF THE INVENTION

The present invention relates to detecting and organizing changes in policies, and more specifically to healthcare policies.

BACKGROUND

A medical manufacturing company that provides pharmaceuticals or medical devices will naturally be interested in which insurance companies provide coverage for its products, as the more insurance companies that provide coverage for the product, the larger the potential customer base is. Healthcare professionals, such as medical manufacturing companies, currently rely on a cumbersome manual system of determining if healthcare insurance policies have been updated or changed. However, most healthcare professionals find out about changes to an insurer's coverage policies passively through newsletters and the like, or anecdotally through others in the industry, long after the change has occurred.

The predominant method of keeping track of insurer healthcare updates is to subscribe to newsletters and manually visit websites to see if a change has occurred. This is not an adequate solution due to the time required to visit the voluminous number of websites that carry relevant information and the human error that can miss a change (assuming such a change occurred on the website accessed). Subscribing to newsletters is also inadequate because health insurers do not always update their newsletters comprehensively, nor release them on a regular schedule; and newsletters are frequently released long after a change has actually occurred. It is thus important for stakeholders to find out about a change in policy as quickly as possible after it occurs.

Generic software crawling technology is available, but is not targeted specifically towards the healthcare industry and the needs of medical device manufacturers, pharmaceutical manufacturers, diagnostic companies, dental device manufacturers, professional healthcare associations and insurance companies; and offers no organization once a change is detected.

A proposed solution exists that offers a query based database that contains names of health plans of tiers of pharmaceuticals, but fails to offer a database of update notifications and does not include information on medical devices; only pharmaceuticals.

Another proposed solution offers an alert service for healthcare policy websites, but does not provide an analytical database that can customize, target and sort information within a policy or policy change, including information such as prior authorization requirements and current procedural terminology coding, and fails to provide a corresponding analytical tool.

Other services provide a similar function but lack a targeted organized database of information that can be accessed via multiple searches and targeted data queries and are unable to produce customized reports that are updated along with the changes produced by a computer system.

Another proposed solution is found in U.S. Patent Application Publication No. 2011/0112873 disclosing a system and method for electronically monitoring, alerting and evaluating changes in a health care payor policy.

SUMMARY OF THE INVENTION

The system according to the invention scans a large volume of information available in a database of downloaded websites and documents, which are available through the Internet, to detect targeted changes related to healthcare insurance policies, using criteria selectable by a user. The information is then condensed to a format that is easily ported into a second database that houses and organizes the new information. The second database is accessible by the user and drop down menus are available to allow the user to generate a report displaying selected elements of healthcare policies in rows, with the name of the insurer in the column headings. The system according to the invention can use multiple servers to scan websites to collect and process large volumes of information.

The system can allow stacking of servers, so all servers contribute to the singular data output produced by the main server. Each server can act independently of the others so disruption to a single server does not affect any processes or jobs of other servers.

The system and method according to the invention solves the problem of scanning a huge web domain of information that could not be done completely in a manual fashion, multiple times a day. With the system, any changes to healthcare policies are detected no less than 24 hours after being posted on the web. A user interface that sorts the information allows ease of use and readability. By porting the information into a second database where it is organized and queried with a user-driven analytical tool, users gain additional insight into each policy and can compare consistent features of each policy across multiple insurance payers. This automated database provides the payer names as the columns, under which are healthcare policy specific data components (such as therapy coverage, prior authorization, previous and next review dates, coding).

Multiple computer servers can be used to detect changes in a database of policies relevant to each user and to continually scan the websites in which the policies are located to download the policies into the database and capture the changes, which undergo further processing before the information is presented to the user.

The system allows users to receive change updates to their policies of interest, without having to continually and manually log into each insurer's website and determine if there is a change. The system has the ability to capture insurance policy information from insurers and health technology assessments in the US, Europe, Latin America, Canada and other countries around the world.

The system is designed to specifically target predefined medical therapies in a designated database of websites for easy software based manipulation of change data.

The system creates value for the user as the user can pick out changes to a volume of documentation that is impossible to scan efficiently through human effort alone. The system also removes the element of human error when determining if a document has changed. The user enjoys the benefit of having change information delivered to them much quicker than passively waiting for inconsistent and unreliable newsletter announcements from insurers (every insurer has disparate procedures in releasing newsletters, and many do not release them at all). Additional value is offered in a second database that houses much of the change information in a format that allows querying of specific data within policies, allowing the user to produce a report comparing this data across multiple insurers of their choosing.

The system can alert the user to changes in documentation automatically via email, Short Message Service (SMS) or mobile application push notifications, thereby allowing the user to keep apprised of changes daily.

A method of providing changes in healthcare policy information is provided, including: providing a first database, the first database containing a plurality of records, each record containing a copy of a website, the website pertaining to healthcare policy information; scanning current versions of the websites on the Internet and determining which of the websites have changed by comparing the current version of the website on the Internet to the copy in the first database; then identifying the website to a first server; and updating the copy of the website in the first database; and providing access to reports generated to reflect changes in the website.

The first server may determine the changes made to each of the websites identified by a second server that scans the current versions of the websites. Records including the changes made to each of the websites identified by the second server may be stored in a second database. A first user interface may allow a user to search the first database. The second database may be searchable by the user through a second user interface.

A field of each record in the first database may include at least one of the fields selected from the following: procedure name, medical device name, diagnostic test name, guideline name, vaccine name, drug name; name of insurer; and health plan name. A field of each record in the second database may include at least one of the fields selected from the following: procedure name, medical device name, diagnostic test name, guideline name, vaccine name, website name; insurer name; and coverage criteria.

A system for managing healthcare policy information is provided, including: a first database, the first database containing records including copies of websites, the websites pertaining to policy information; a first server configured to scan current versions of the websites on the Internet and identifying which of the current websites have been changed since a previous scan of the website to a second server; and updating the records in the first database; and a second server configured to generate a report of the changes made to each of the identified websites; the second server also configured to provide access to a user to generate reports relating to the websites.

The second server may be configured to determine the changes made to the websites identified by the first server and to generate an alert for a user on a change to a preselected website, the alert including information about the change to the preselected website. The system may include a mobile device application connected to the first database and the second database thereby allowing users to access and interact with healthcare policy data stored on the first and second databases.

A system for viewing healthcare policy information is provided, including: a database containing a plurality of websites, the websites corresponding to copies of websites pertaining to healthcare insurance coverage policies; a second database of user selectable data fields containing elements of websites stored in the first database; a user interface whereby a user can view and download healthcare insurance coverage information related to the healthcare insurance coverage policies, the policies sortable by procedure name, medical device name, diagnostic test name, guideline name, vaccine name, website name; insurer name; and coverage criteria; a server in communication with the first and second databases, the server configured to generate data output from criteria selectable by the user through interactive menus; and means for exporting the data output into a selected data formats.

DESCRIPTION OF THE FIGURES

FIGS. 5a and 5b show an embodiment of a user interface whereby a user can select data for display.

DETAILED DESCRIPTION OF THE INVENTION

Figure 1:
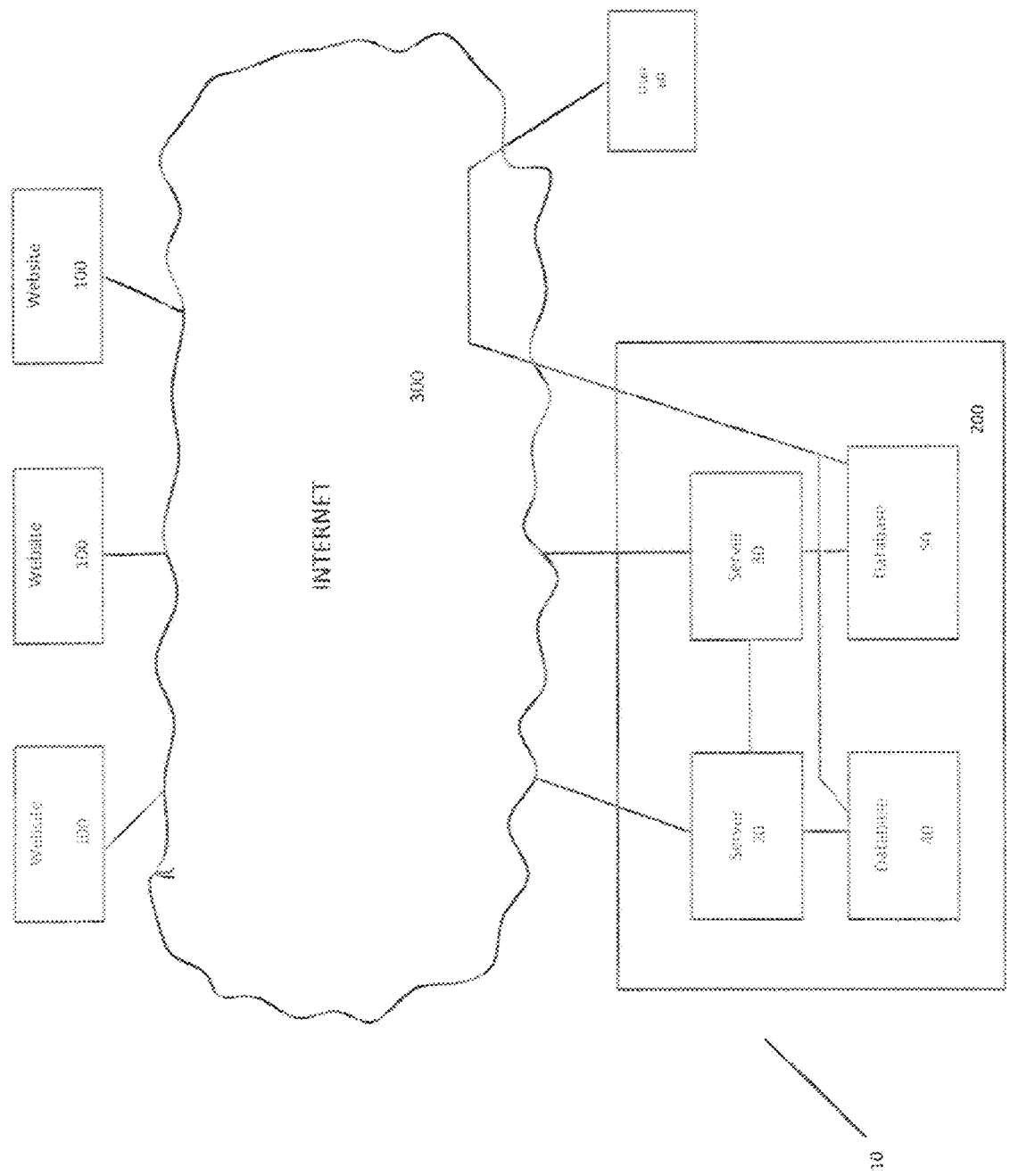
FIG. 1 is a block diagram showing an overview of an embodiment of a system according to the invention.

As shown in FIG. 1, system 10 includes first and second servers 20 and 30, and first and second databases 40 and 50. First server 20 is in communication with a plurality of healthcare policy websites 100 through a network, such as the Internet 300. First server 20 uses software to scan specified websites having such healthcare policies, and communicates with first database 40 to determine if changes have occurred. Users 60 communicate with second database 50 through a network, such as the Internet 300, to access first database 40 and second database 50.

Figure 2:
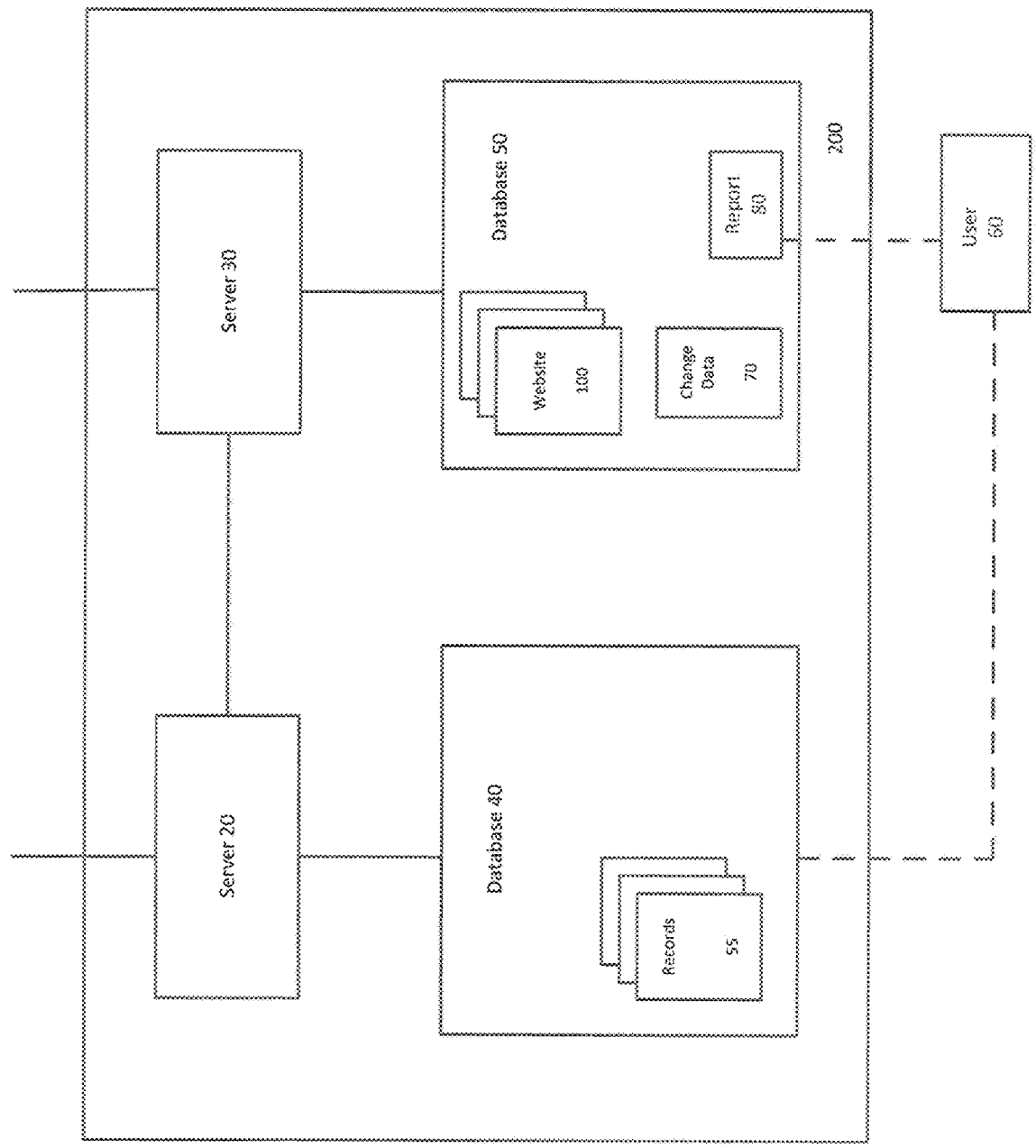
FIG. 2 is a block diagram showing the databases and servers in an embodiment of a system according to the invention.
Figure 3:
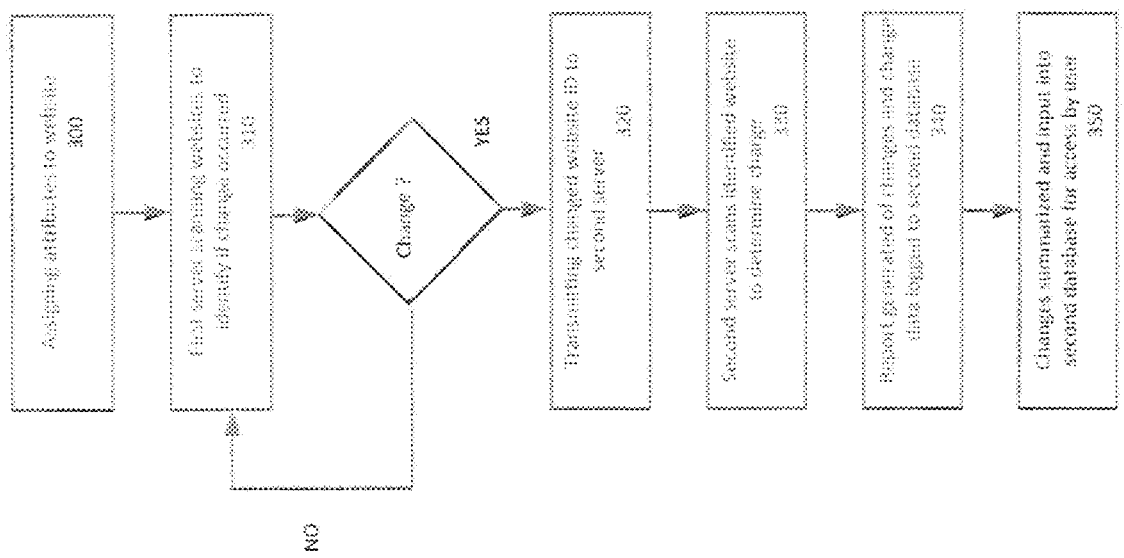
FIG. 3 is a flow chart showing the steps taken in an embodiment of a method according to the invention.

As shown in FIG. 2, database 40 contains records 55 of the text of each healthcare policy website 100 being tracked (websites 100 are selectable by user 60 to allow user 60 to determine which have changed). Records 55 may first be collected by server 20 and then copied and input into database 40 via the computer system 200 administrator backend. As shown in FIG. 3, in use of the system, specific attributes and serial ID fields are assigned to records 55 for each healthcare policy website 100 for future sorting and searching (step 300); some of these fields may include Title of Website, Disease State, Treatment Method, Drug Name, Formulary Name, Prior Authorization Form Name, Guideline Name, Immunization Schedule Name, Health Plan Name, and Name of Insurer. An administrator may specify features of each website 100 to increase readability of the underlying code to be scanned by the software script (e.g. designate the website as an .html or .pdf file).

First server 20 then uses software to scan each website 100 identified in database 40 of websites 100 on a predetermined schedule (for example once or more per day depending on capacity) to determine if any changes to the text, code or document file size of the website has occurred by comparing the text at website 100 accessible on the Internet and being scanned to the most recent version of the text at the website stored in database 40 (step 310) in the appropriate record 55. Websites 100 with text that is identified as having been changed are recorded by serial ID and that information (i.e. that a change has occurred) is automatically transmitted to second server 30 (step 320). Websites 100 with text that has not changed are passed over and remain on the schedule to be reviewed again the next day, or the next timeslot if the scan occurs more than once a day.

Second server 30 receives the serial ID information of websites 100 that have changed and then downloads only those websites 100 to determine the exact nature of the change (step 330). Second server 30 downloads data and documents from healthcare policy websites in multiple formats including but not limited to HTML, XML, .PHP, .PDF, .DOC, JavaScript, AJAX, and .ASP, and records the data and text in the database. Second server 30 then runs a server-side script to compare the existing data in the database with the newly downloaded data and generates a report to the administrator backend indicating the text that was added or removed from the document or file at the website 100, by serial ID (step 340). The differences in the text from the previous text stored in record 55 is referred to as change data.

Figure 6:
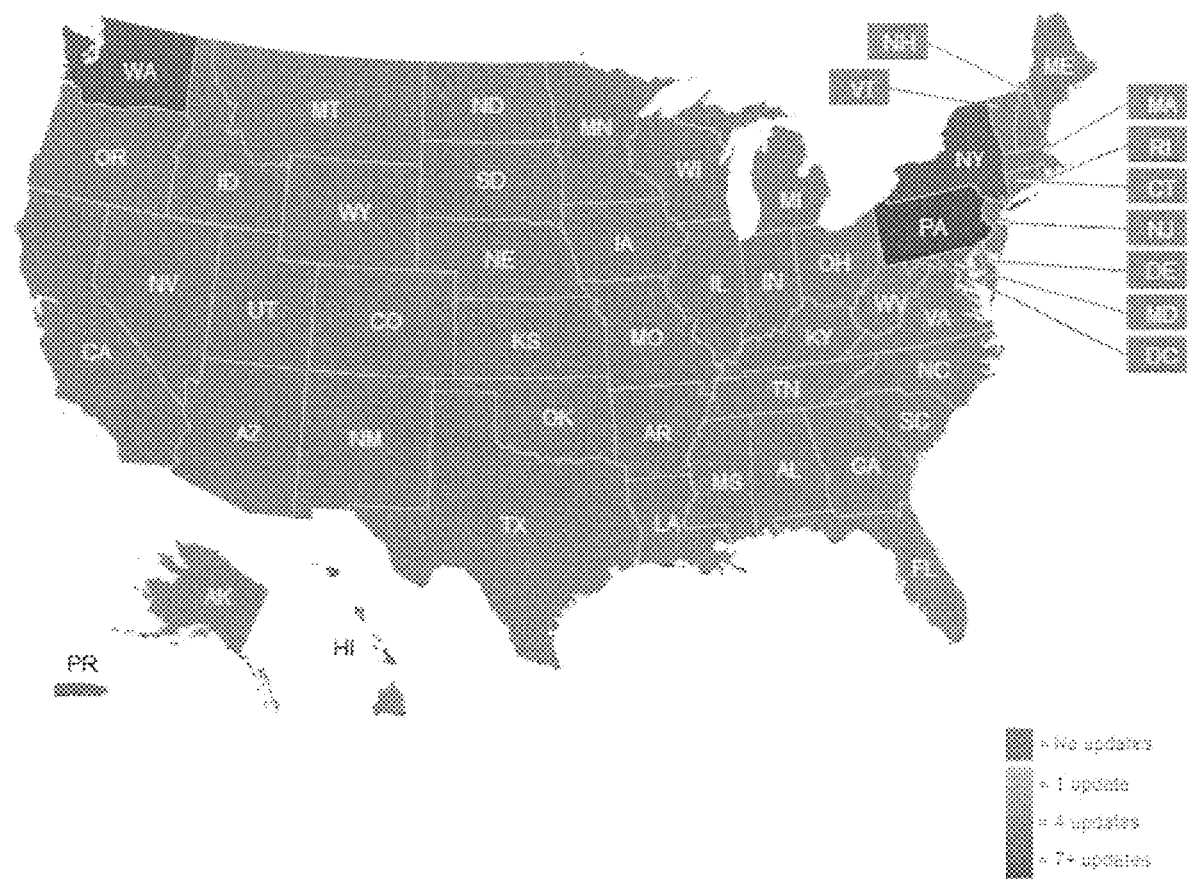
FIG. 6 shows an embodiment of a map displayable to users

The system scans and detects websites by URL, groups all websites that look identical, and labels them as "root" for the original website and "children" for all subsequent websites identical to the root. For all future scans, the system may scan only the root website, and attribute the result data to all the children websites to decrease server load. The system, through a script, automatically runs metrics on the quantity of changes attributed to a particular payer based on changes in the text from website 100, and then can display the information on a color coded graphical map, as shown in FIG. 6, which shows the concentration of changes of payer policies between various geographic regions.

Figure 4A:
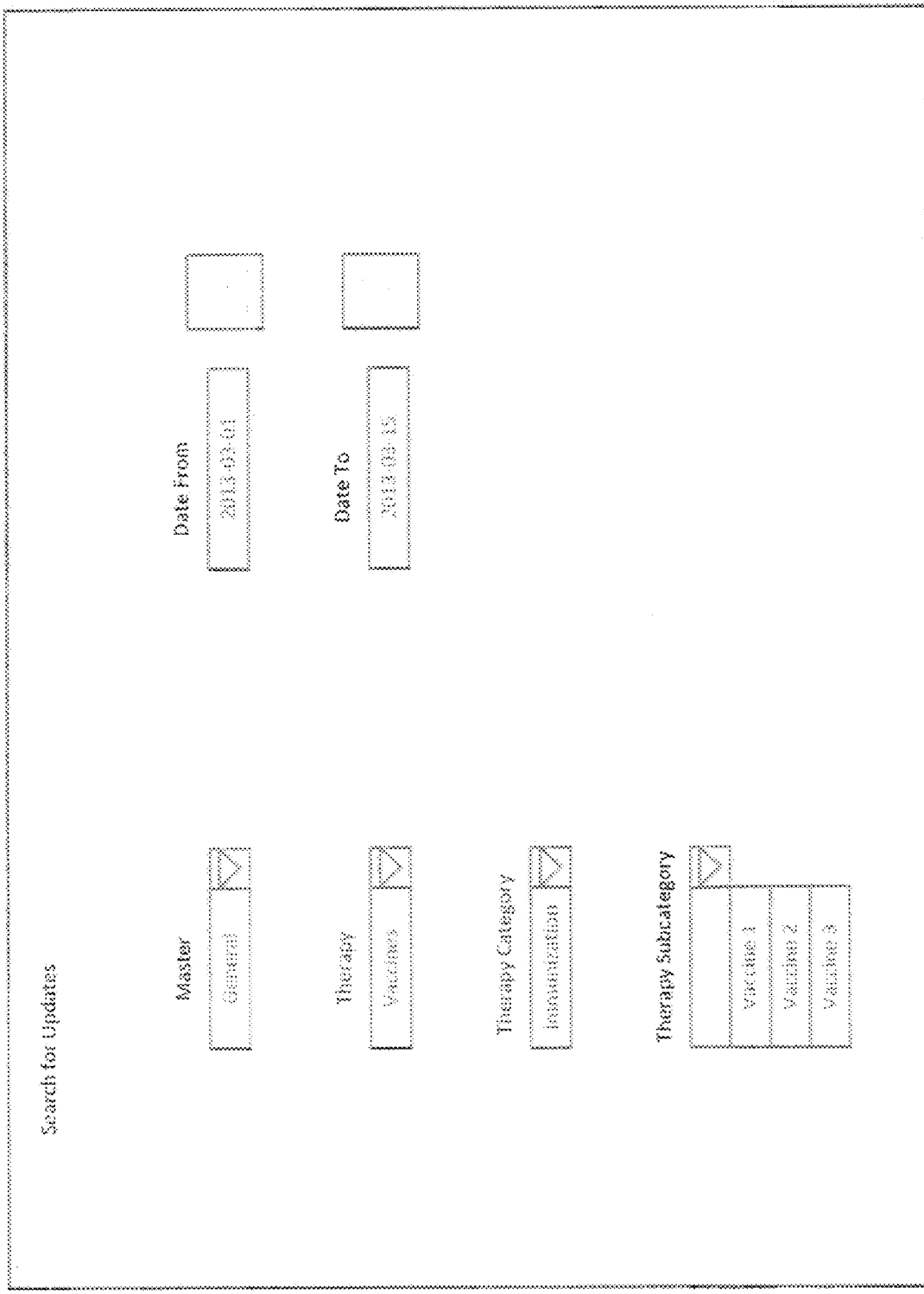
FIGS. 4a and 4b show an embodiment of a user interface whereby a user can determine if changes have been made to a policy.
Figure 4B:
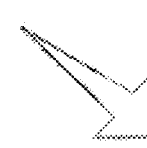

The change data 70 is automatically saved and logged into second database 50, and becomes searchable by a user based on a number of fields, including the date the change occurred, and the attributes and fields originally designated to the specific document and/or website 100 input into first database 40. This information is searchable via a user interface accessible, as shown in FIG. 4*a*, by user 60 who can search change information by the specific attributes, as well as the data within the site in which the change occurred. The result of a query by the user 60 is shown in FIG. 4*b*. In the example shown a change to Gardisil policy has occurred and CPTs 90649 and 90650 are no longer covered, which is conveyed to the user in a pop up box displayed when the user clicks on, touches, scrolls over or otherwise indicates the change summary area.

The text that is added in the new version of the website 100 is stored in a text file in one column, separated by line. The text that is removed in the previous version of website 100 stored in database 40 is stored in the same text file in a separate column, separated by line. Changes to text in a policy can be displayed to user 60 this way, or in a variety of other ways. In another embodiment, new text may be indicated with underlining and removed text shown as struck though.

The user may be notified through an automated system operated by one or both of first server 20 and second server 30 about changes to preselected websites. The system can send specific policy information contained in the databases via email, Short Message Service (SMS) or mobile application push notification to the user. The change data, the insurer name and additional data elements may be contained within the message to user 60 and/or a link to the information can be included. Users may subscribe, via an administrative interface, to specific types and sub-types of messages and reports they would like to receive.

The newly updated website 100 is then analyzed and certain components of it may be summarized and ported to and saved at a second database 50, to be available for use as an analysis tool for the end user (step 350). Most insurer health policy websites 100 include common components for fields such as: Insurer Name; Website Name; Coverage Criteria; Prior Authorization; Previous and Next Review Dates; Coding; Background; Copay; Drug Tier Status; Preferred Pharmacy; Preferred Clinic; Preferred Physician Network; Health Plan; Coverage age range of patient; "Try and Fail" drug criteria; Conservative therapy criteria; clinical study lists; covered lives; and References. These fields may be autopopulated (for example using keywords), summarized, and input into corresponding fields of the administrative interface of the second database 50.

The user 60 can search database 50 by one or any of the aforementioned fields and select the insurer with which he or she wants to compare data, as shown in FIGS. 5*a* and 5*b*. For example, user 60, using the interface shown in FIG. 5*a*, may wish to compare coverage criteria and coding (or any combination of the inputted fields) for a number of insurers of their choosing (selectable from a dropdown menu). A report 80, an embodiment of which is shown in FIG. 5*b*, is then generated displaying the data, with the insurer names as column headings, and the selected fields as rows. Both headings and rows are sortable alphabetically and numerically. This table is then exportable into multiple file formats (.txt, .csv, .xlsx., .xls, .doc., .docx) for download by user 60.

A mobile application, accessible and executable on a mobile device, connects to both databases and allows the user to access a separate mobile user interface. The mobile user interface allows the user to access the change data, search the website and document database and generate reports with optimized display, formatting and data output for various mobile devices, such as smart phones and tablets.

The embodiments and techniques described above may be implemented as a system or plurality of systems working in conjunction, or in software as various interconnected functional blocks or distinct software modules. This is not necessary, however, and there may be cases where these functional blocks or modules are equivalently aggregated into a single logic device, program or operation with unclear boundaries. In any event, the functional blocks and software modules implementing the embodiments described above, or features of the interface can be implemented by themselves, or in combination with other operations in either hardware or software, either within a device entirely, or in conjunction with the device and other processer enabled devices in communication with the device, such as one or more additional servers.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

What is claimed is:

1. A computer-implemented method of tracking changes in healthcare policy documents, using a computer system, the method comprising:
providing, in the computer system, a first database containing a plurality of records, each record containing a copy of a website from which original healthcare policy documents are located and downloaded into the first database;
assigning a serial ID and a field to each record;

scanning on a predetermined schedule, using a first server, current versions of the web sites on the Internet to identify which of the current websites have been changed in text, code, or document file size since a previous scan of the websites by comparing the text of the websites on the Internet to the text of the web sites stored in the first database; and updating the records in the first database;

transmitting the serial IDs of the identified web sites having changes to a second server and scheduling websites which are unchanged for re-scanning;

scanning on a predetermined schedule, using the second server, the identified websites from which updated healthcare policy documents are downloaded and compared to the original healthcare policy documents in the first database to capture changes made to the original healthcare policy documents, wherein the second server runs a server-side script to determine the changes in the form of text that was added or removed from each of the updated healthcare policy documents and generates a report indicating the text that was added or removed by the serial IDs; wherein scanning comprises detecting the identified websites by URL, grouping the identified websites, labelling the identified websites as either original websites or subsequent websites, and scheduling the original websites for re-scanning and attributing result data to the subsequent websites to decrease server load;

running metrics on quantity of changes attributed to an insurer based on the changes in the text from the identified websites, and displaying a map showing concentration of changes in the healthcare policy documents across geographical regions;

storing records including the changes made to each of the updated healthcare policy documents identified by the second server in a second database;

providing a user device comprising a smartphone, a tablet, or a personal computer running an application connected to the first and second databases;

allowing a user to use the smartphone, the tablet, or the personal computer to search the first and second databases and to generate reports; and displaying the reports comprising a visualization of the changes to the text in the healthcare policy documents on the smartphone, the tablet, or the personal computer to the user, and healthcare policy specific data components selected by the user of healthcare policies in rows and a name of an insurer in column headings, allowing the user to compare consistent features of each healthcare policy across a plurality of insurers.

2. The method of claim 1 further comprising a first user interface, the first user interface configured to allow the user to search the first database.

3. The method of claim 2 wherein the second database is searchable by the user through a second user interface.

4. The method of claim 3 wherein a field of each record in the first database includes at least one of the fields selected from the following: procedure name, medical device name, diagnostic test name, guideline name, vaccine name, drug name; name of insurer; and health plan name.

5. The method of claim 4, wherein a field of each record in the second database includes at least one of the fields selected from the following: procedure name, medical device name, diagnostic test name, guideline name, vaccine name, website name; insurer name; and coverage criteria.

6. A non-transitory computer-readable medium carrying computer-executable instructions for tracking changes in healthcare policy documents, the instructions being executable by a processor to:

access a memory storing a first database, the first database containing records including copies of websites from which original healthcare policy documents are located and downloaded into the first database;

assign a serial ID and a field to each record;

request a first server to scan on a predetermined schedule current versions of the websites on the Internet and identify which of the current websites have been changed in text, code, or document file size since a previous scan of the websites by comparing the text of the websites on the Internet to the text of the web sites stored in the first database; and update the records in the first database;

transmit the serial IDs of the identified websites having changes to a second server and schedule websites which are unchanged for re-scanning;

request the second server to scan on a predetermined schedule the identified websites from which updated healthcare policy documents are downloaded and compared to the original healthcare policy documents in the first database to capture changes made to the original healthcare policy documents, wherein the second server runs a server-side script to determine the changes in the form of text that was added or removed from each of the updated healthcare policy documents and generates a report indicating the text that was added or removed by the serial IDs; wherein scanning comprises detecting the identified websites by URL, grouping the identified websites, labelling the identified websites as either original websites or subsequent websites, and scheduling the original websites for re-scanning and attributing result data to the subsequent websites to decrease server load; run metrics on quantity of changes attributed to an insurer based on the changes in the text from the identified websites, and displaying a map showing concentration of changes in the healthcare policy documents across geographical regions; and store the changes made to each of the updated healthcare policy documents in a second database;

request the second server to generate a report of the changes made to the healthcare policy documents; the second server also configured to allow a user to search the first and second databases and generate reports, wherein the second server is configured to determine the changes in the form of text that was added or removed from each of the updated healthcare policy documents from the websites identified by the first server; and displaying the reports comprising a visualization of the changes to the text in the healthcare policy documents and healthcare policy specific data components selected by the user of healthcare policies in rows and a name of an insurer in column headings to allow the user to compare consistent features of each healthcare policy across a plurality of insurers, to the user on a user device comprising a smartphone, a tablet, or a personal computer running an application connected to the first and second databases.

7. The non-transitory computer-readable medium of claim 6 wherein the second server is configured to generate an alert for the user on a change to a preselected website, the alert including information about the change to the preselected website.

8. The non-transitory computer-readable medium of claim 6 further comprising a mobile device application connected to the first database and the second database thereby allowing users to access and interact with healthcare policy data stored on the first and second databases.

* * * * *